United States Patent
Nakamura

(10) Patent No.: US 6,932,806 B2
(45) Date of Patent: Aug. 23, 2005

(54) METHOD FOR ASSESSING IRRADIATION INTENSITY OF A LASER BEAM, AN APPARATUS FOR ASSESSING IRRADIATION INTENSITY USED UNDER THIS METHOD, AND A LASER BEAM IRRADIATION SYSTEM

(75) Inventor: Takua Nakamura, Hoi-gun (JP)

(73) Assignee: Nidek Co., Ltd., Gamagori (JP)

( * ) Notice: Subject to any disclaimer, the term of this patent is extended or adjusted under 35 U.S.C. 154(b) by 247 days.

(21) Appl. No.: 10/080,712

(22) Filed: Feb. 25, 2002

(65) Prior Publication Data

US 2002/0120198 A1 Aug. 29, 2002

(30) Foreign Application Priority Data

Feb. 28, 2001 (JP) ........................................ 2001-055771

(51) Int. Cl.⁷ ................................................ A61F 9/008
(52) U.S. Cl. .......................................................... 606/5
(58) Field of Search ................................ 606/5, 10–13, 606/17

(56) References Cited

U.S. PATENT DOCUMENTS

| | | |
|---|---|---|
| 5,507,799 A | 4/1996 | Sumiya |
| 5,520,679 A | 5/1996 | Lin |
| 5,556,395 A | 9/1996 | Shimmick et al. |
| 5,637,109 A | 6/1997 | Sumiya |
| 5,713,893 A * | 2/1998 | O'Donnell ................... 606/10 |
| 5,827,264 A | 10/1998 | Hohla |

FOREIGN PATENT DOCUMENTS

| | | | |
|---|---|---|---|
| CA | 2065174 | * 4/1992 | ................... 606/10 |
| EP | 1 040 797 A2 | 10/2000 | |
| EP | 1 040 797 A3 | 10/2001 | |

* cited by examiner

*Primary Examiner*—David M. Shay
(74) *Attorney, Agent, or Firm*—Oliff & Berridge, PLC

(57) ABSTRACT

The present invention intends to provide a method with a relatively uncomplicated mechanism, for assessing irradiation intensity of a laser beam, whereby an operator can accurately assess irradiation intensity of the laser beam, and to provide an apparatus used through this method. The method for assessing irradiation intensity of a laser beam includes steps of irradiating the laser beam onto a reference object on which a change in its state is caused by irradiating the laser beam, and a light quantity of transmitted light of specified illumination light changes in accordance with an irradiation energy density of the laser beam when the illumination light is projected, obtaining an image formed by a change in the light quantity of the transmitted light, occurring when the illumination light is projected on the reference object having been irradiated by the laser beam, and analyzing a condition of the change in the reference object based on the obtained image, wherein an irradiation intensity distribution of the laser beam is assessed based on an analytical result.

10 Claims, 8 Drawing Sheets

METHOD FOR ASSESSING IRRADIATION INTENSITY OF A LASER BEAM, AN APPARATUS FOR ASSESSING IRRADIATION INTENSITY USED UNDER THIS METHOD, AND A LASER BEAM IRRADIATION SYSTEM

BACKGROUND OF THE INVENTION

1. Field of the Invention

The present invention relates to a method for assessing irradiation intensity of a laser beam irradiated onto an object, an irradiation intensity assessment apparatus used under this method, and a laser beam irradiation system.

2. Description of Related Art

Laser beams are used in various fields such as for medical treatment and processing materials and the like. As an ophthalmological laser irradiation apparatus, for example, such has been known that an operator irradiates an excimer laser beam using an apparatus to ablate an epithelium and a corneal stroma of a patient's eye to change corneal curvature for correcting a refractive error such as myopia or to ablate an affected area of a corneal surface. As for this type of the apparatus, it is considered important to arrange the apparatus so that ablation depth is approximately uniform on an object to be irradiated. European Patent Application publication No. EP1040797 corresponding to Japanese Patent Application Unexamined Publication No. 2000-279440 should be referred, wherein the present applicant discloses a laser irradiation apparatus configured in such a manner that laser beam irradiation density within an ablation region is changed so that the operator ablates an object approximately uniformly using the apparatus.

Incidentally, although adjustment for accomplishing approximately uniform ablation is carried out at the time of manufacturing a laser irradiation apparatus, an ablation depth on the object to be irradiated may change when optical elements are set at a site for installing the laser irradiation apparatus. This change may be caused by an influence of a delicate alignment adjustment of optical axes. The ablation depth on the object to be irradiated may also change because of deterioration due to a change over time in an optical element disposed in an irradiating optical system. Thus, at the site for installing a laser irradiation apparatus, prior to actual laser irradiation on an object to be processed (treated), it is necessary to irradiate a laser beam on a reference object for assessment and adjust irradiation intensity of the laser beam based on the examination of the ablation depth.

Conventionally, as for a simplified method for examining an ablation depth, such has been conducted that after irradiating a laser beam on a transparent polymethyl methacrylate (PMMA) plate in a certain irradiation condition and ablating the plate, a change in a refractive power on the PMMA plate is read using a lens meter. Further, detailed data on the ablation depth are obtained by analyzing the ablated PMMA plate using a three-dimensional shape analyzing apparatus.

An examination using a lens meter is relatively easily carried out at the site where a laser irradiation apparatus has been installed. However, it merely gives general information about the ablation depth, and it does not give the details. On the other hand, when a three-dimensional analyzing apparatus is used, the apparatus is large-scale and pricey, and its transportability is low. Therefore, there may be occasions when using the three-dimensional analyzing apparatus is not easy at the site for installing a laser irradiation apparatus.

SUMMARY OF THE INVENTION

The present invention has been made in view of the above circumstances and has an object to overcome the above problems and to provide a method with a relatively uncomplicated mechanism, for assessing irradiation intensity of a laser beam, whereby an operator can accurately assess irradiation intensity of the laser beam, and to provide an apparatus used through this method.

To achieve the objects and in accordance with the purpose of the present invention, as embodied and broadly described herein, a method for assessing irradiation intensity of a laser beam includes steps of irradiating the laser beam onto a reference object on which a change in its state is caused by irradiating the laser beam, and a light quantity of transmitted light of specified illumination light changes in accordance with an irradiation energy density of the laser beam when the illumination light is projected, obtaining an image formed by a change in the light quantity of the transmitted light, occurring when the illumination light is projected on the reference object having been irradiated by the laser beam, and analyzing a condition of the change in the reference object based on the obtained image, wherein an irradiation intensity distribution of the laser beam is assessed based on an analytical result.

In another aspect of the present invention, an apparatus for assessing irradiation intensity of a laser beam comprises a reference object on which a change in its state is caused by irradiating the laser beam, and a light quantity of transmitted light of specified illumination light changes in accordance with an irradiation energy density of the laser beam when the illumination light is projected, an image obtaining device which obtains an image formed by a change in the light quantity of the transmitted light, occurring when the illumination light is projected on the reference object having been irradiated by the laser beam, and an analyzing device which analyzes a condition of the change in the reference object based on the obtained image, wherein an irradiation intensity distribution of the laser beam is assessed based on an analytical result.

Yet, in another aspect of the present invention, a laser beam irradiation system comprises an irradiation optical system for irradiating a laser beam onto an object to be irradiated, a reference object on which a change in its state is caused by irradiating the laser beam, and a light quantity of transmitted light of specified illumination light changes in accordance with an irradiation energy density of the laser beam when the illumination light is projected, an image obtaining device which obtains an image formed by a change in the light quantity of the transmitted light, occurring when the illumination light is projected on the reference object having been irradiated by the laser beam, an analyzing device which analyzes a condition of the change in the reference object based on the obtained image, and a control device which obtains control data for the system so that the object to be irradiated achieves a condition of a desired change based on an analytical result from the analyzing device.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
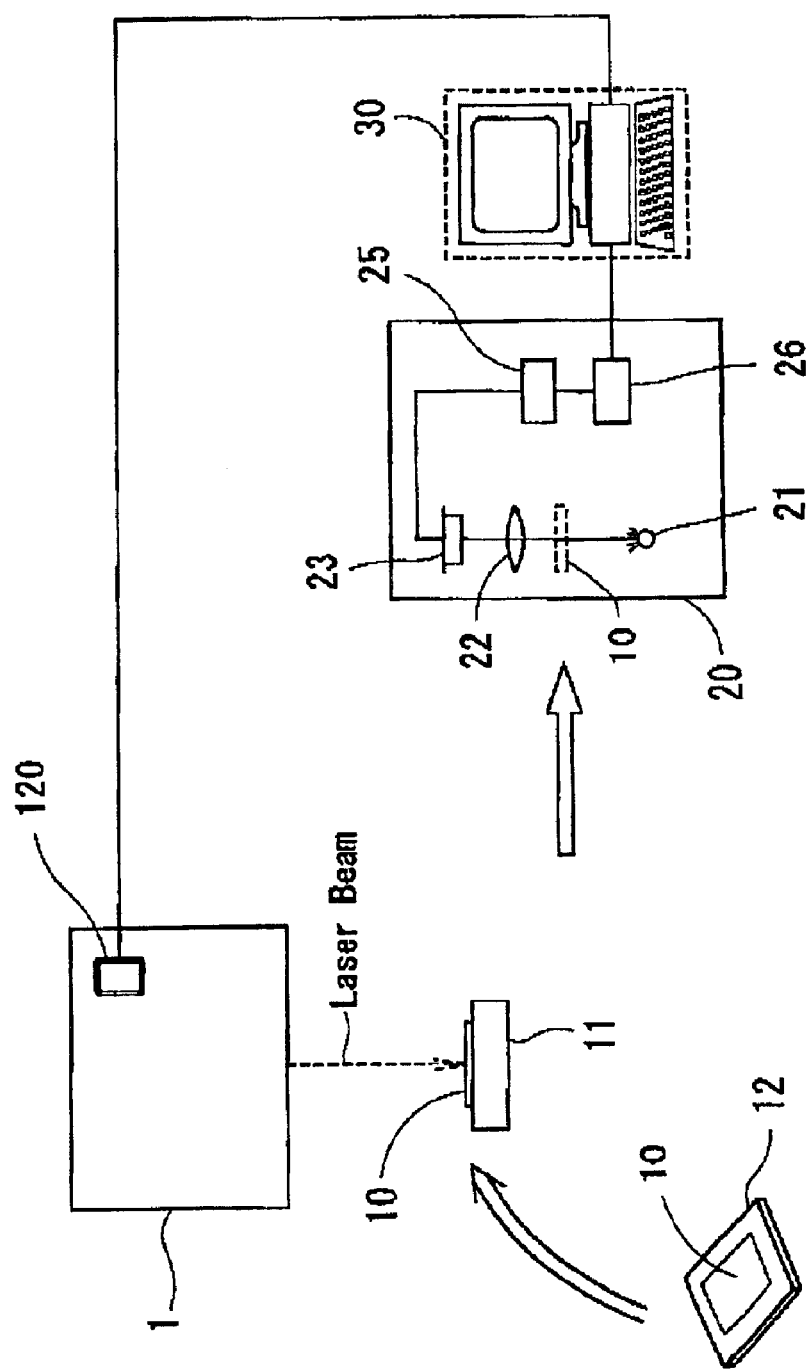
FIG. 1 is a view showing a schematic configuration of a laser irradiation system consistent with the present embodiment of the present invention.

A detailed description of one preferred embodiment of a method for assessing irradiation intensity of a laser beam, an irradiation intensity assessment apparatus used under the method, and a laser beam irradiation system embodying the present invention will now be given referring to the accompanying drawings. FIG. 1 is a view showing a schematic configuration of a laser irradiation system consistent with the present invention.

A laser irradiation apparatus 1 is designed to ablate a cornea by an excimer laser beam. An unexposed positive film 10 having been developed is a reference object for assessing laser irradiation intensity. As the reference object for assessing irradiation intensity of the excimer laser beam, such should be used that the excimer laser beam ablates the reference object to produce a gradation contrast change thereon due to a difference in a condition of an energy density distribution of the irradiated laser beam. That is, it is preferable to use a film-type reference object in which light quantity of its transmitted light changes in accordance with irradiation energy density of the laser beam when specific illumination light is projected. In the present embodiment, the positive film 10 commercially available for photographing is used so that it is easily obtained even in medical facilities where the laser irradiation apparatus 1 is to be installed. A gradation contrast change is produced on the film 10 in accordance with an ablation depth. A base 11 where the positive film 10 is placed may be in any configuration if it can stably hold the film 10 thereon during laser irradiation. Having been cut in a proper size, the positive film 10 is placed in a mount 12 generally used for a photo slide. Then, the mount 12 is positioned on the base 11.

An image scanner 20 reads a gradation contrast change on the positive film 10. The image scanner 20 includes a light source 21 illuminating the positive film 10 disposed at a specified position, CCD 23 (photographic element) photographing via a lens 22 light having been transmitted through the positive film 10, an image memory 25 storing a photographed image, and a control part 26 controlling operations of the image scanner 20. Commercially available image scanners may be used as the image scanner 20 for reading an image on the positive film 10.

Commercially available personal computers may be used as an analyzing device 30 connected to the image scanner 20. The analyzing device 30 includes a program for analyzing a gradation contrast change based on the image on the positive film 10 obtained by the image scanner 20. Furthermore, the analyzing device 30 is connected to a control device 120 in the laser irradiation apparatus 1, and the control device 120 obtains control data on laser irradiation based on an analytical result from the analyzing device 30.

Figure 2:
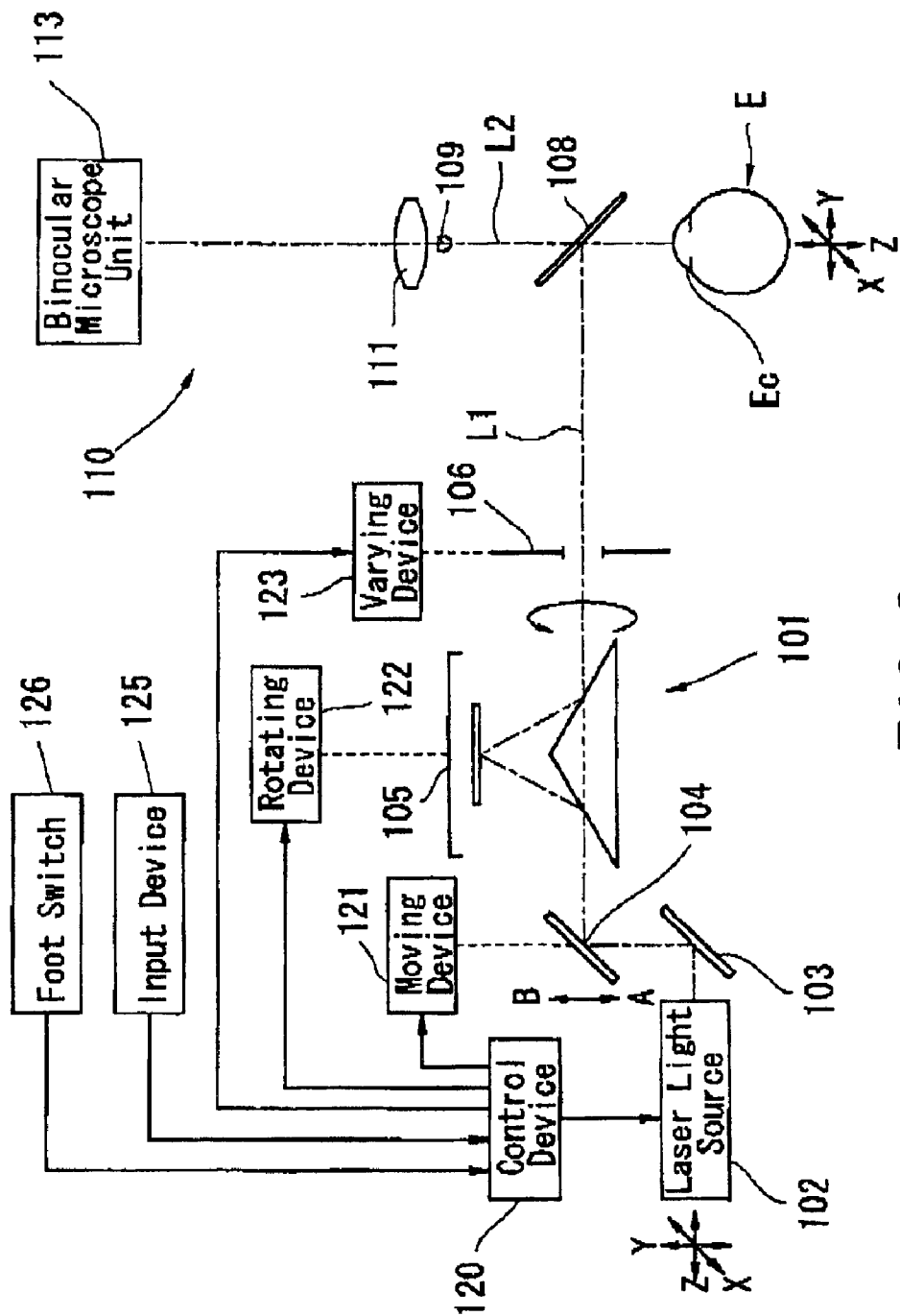
FIG. 2 is a view showing a schematic configuration of optical and control systems in the laser irradiation apparatus.
Figure 3:
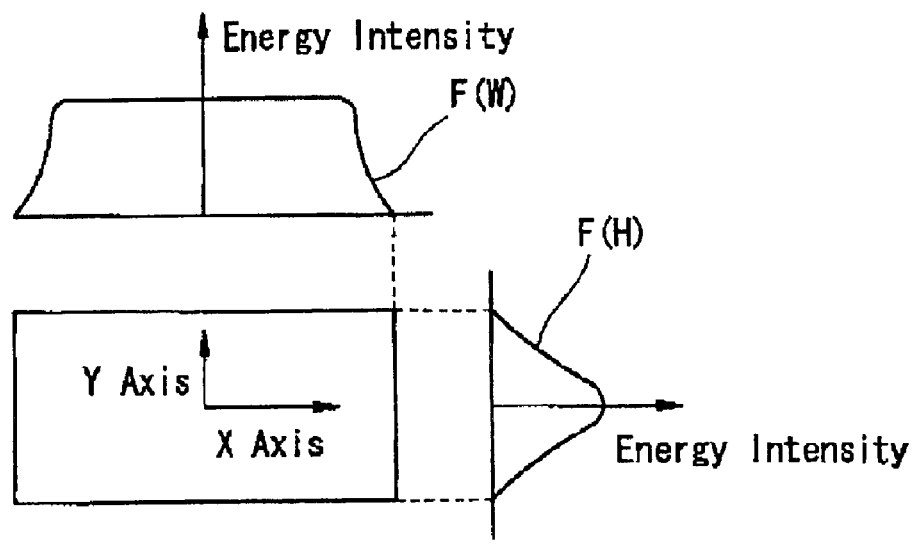
FIG. 3 is a view showing energy intensity distributions of an excimer laser beam emitted from an excimer laser source.

FIG. 2 is a view showing a schematic configuration of optical and control systems in the laser irradiation apparatus 1. An irradiation optical system 101 is provided for guiding the laser beam to a cornea Ec of a patient's eye E and for irradiating the laser beam thereonto. A laser light source 102 emits an excimer laser (ArF laser) beam with a wavelength of 193 nm by generating a pulse. A perpendicular cross section of the laser beam emitted from the laser light source 102 is rectangular. Its energy intensity distribution takes an approximately uniform distribution F(W) in a longitudinal direction of the cross section (the direction of an X axis) and takes the Gaussian distribution F(H) in a direction orthogonal to the longitudinal direction (the direction of a Y axis) (see FIG. 3).

A plane mirror 103 deflects the laser beam emitted from the light source 102, at an angle of 90 degrees. Then, a plane mirror 104 deflects the light 90 degrees again. Also, the mirror 104 is moved by a moving device 121 in parallel with arrows A and B illustrated in FIG. 2 so that the laser beam scans in the direction of the Gaussian distribution.

An image rotator 105 rotates a direction of a scan with the laser beam, about a primary optical axis L1 of the irradiation optical system 101. The image rotator 105 is rotated by a rotating device 122 at a constant velocity and in a constant direction.

An aperture 106 is provided to restrict a region to be ablated by the laser beam, and its diameter is changed by a varying device 123.

A dichroic mirror 108 makes the primary optical axis L1 of the irradiation optical system 101 coaxial with an optical axis L2 of an objective lens 111 included in an observation optical system 110. The dichroic mirror 108 reflects the excimer laser beam and transmits the visible light. The observation optical system 110 is constituted of the objective lens 111, a binocular microscope 113, and the like, whereby the operator can observe the patient's eye E and the positive film 10. Further, the observation optical system 110 includes an unillustrated target projecting optical system for projecting two slit targets for alignment in an axial direction of the optical axis L2 (the direction of a Z axis).

The control device 120, such as a CPU, controls the laser light source 102, the moving device 121, the rotating device 122, the varying device 123, and the like. An input device 125 is provided for inputting an irradiation condition (condition of a surgical operation) such as an ablation region (ablation diameter) and the ablation depth (irradiation amount). A foot switch 126 gives a signal for instructing laser irradiation.

A description will be given regarding a method for approximately uniformly ablating the object to be irradiated.

The mirror 104 is moved by the moving device 121 in parallel with the direction of the arrows A and B in FIG. 2 so that the laser beam scans in the direction of the Gaussian distribution at a velocity determined based on the repetition frequency of the laser pulse from the laser light source 102. The mirror 104 moves in synchronization with the laser pulse. After one or more pulses are emitted at a certain position, the mirror 104 is moved to the next position. Thereafter, it is moved again after one or more pulses are emitted. The above procedure is repeated across the ablation region restricted by the aperture 106. Then, the direction of scanning is changed by a certain angle per scan.

For the laser irradiation as described above, proper control of a travel velocity (travel amount) of the mirror 104 for each scan makes it possible to change intensity of superimposed laser irradiation on the object to be irradiated. Therefore, it is possible to approximately uniformly ablate the object to be irradiated even in the case where there is such a factor as to change the laser irradiation intensity during the laser irradiation onto the object to be irradiated (reference should be made to European Patent Application Publication No. EP1040797 corresponding to Japanese Patent Application Unexamined Publication No. 2000-279440 for details about the method for the laser irradiation).

Incidentally, as mentioned above, although the laser irradiation apparatus 1 is adjusted at the time of manufacturing so as to approximately uniformly ablate the object to be irradiated, the ablation depth on the object changes due to the following factors: setting each optical element at the site for installing the laser irradiation apparatus 1, deterioration due to a change over time in each of the optical elements (especially a reflective mirror in an optical system is quickly deteriorated at its center) and the like. Therefore, prior to actual ablation of the cornea as the object to be processed (treated), at the site for installing the laser irradiation apparatus 1, laser irradiation intensity should be assessed, and control data on the travel velocity of the mirror 104 should be determined based on the result of the assessment.

Figure 4:
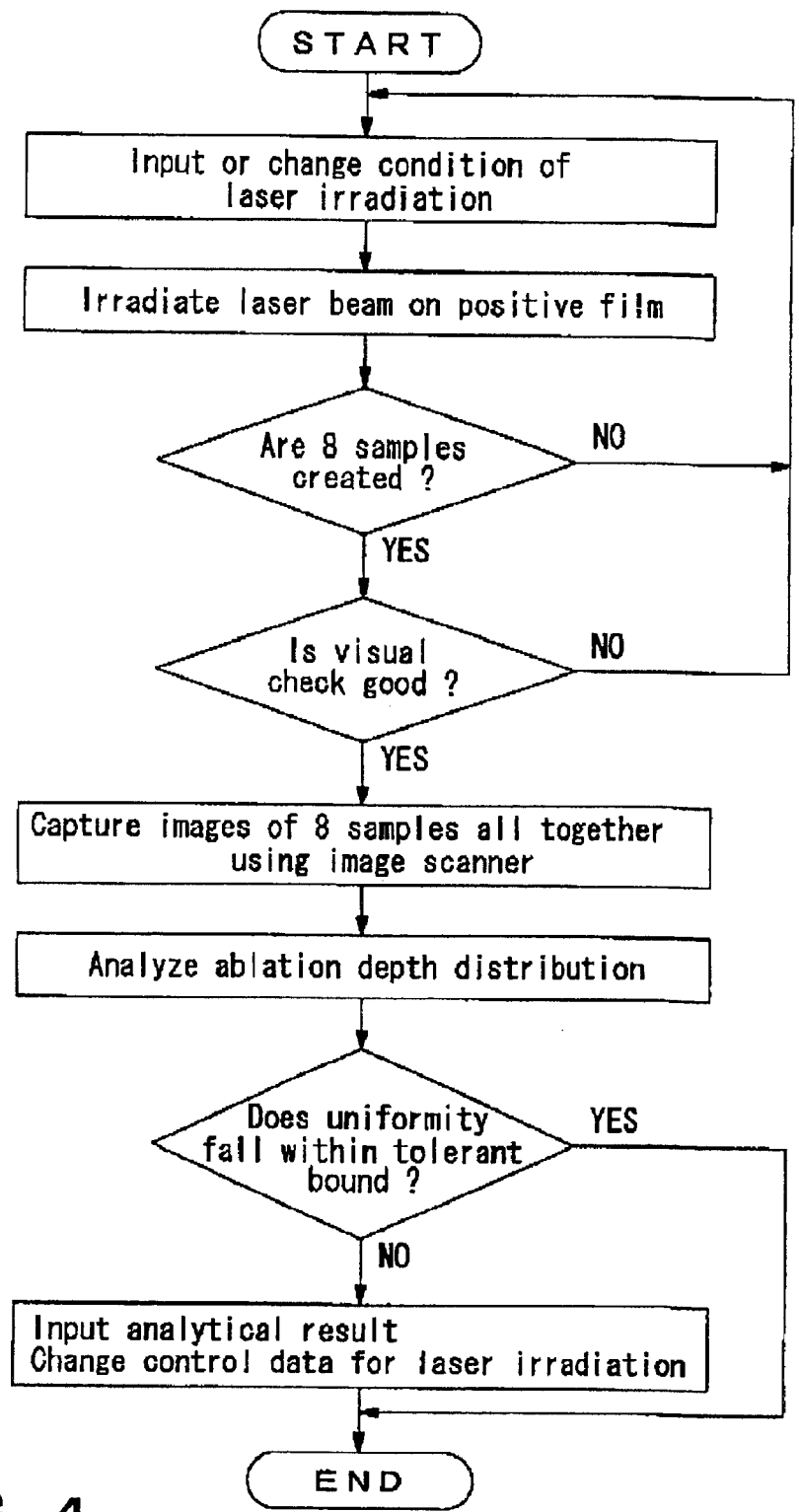
FIG. 4 is a flow chart describing a method for assessing an irradiation intensity distribution.

Next, a description will be given below regarding a method for assessing an irradiation intensity distribution of the laser beam in the system configured in the above manner (see FIG. 4).

First, the laser irradiation apparatus 1 irradiates the laser beam onto the prepared positive film 10 in accordance with a specified irradiation condition so that an irradiation sample is created. It should be noted that the positive film 10 has a region where a gradation contrast change does not proportionally relate to a change in a laser irradiation amount. Therefore, plural irradiation samples receiving different laser irradiation amounts should be created when the positive film 10 is used as a reference object for assessment.

When the irradiation samples are created, an irradiation condition is inputted using the input device 125. In the present embodiment, eight irradiation samples receiving different laser irradiation amounts are created on one positive film 10 in the following way: 8 irradiation samples are created on one positive film 10, and the total number of scanning for each sample varies from 28 to 35.

Figure 5:
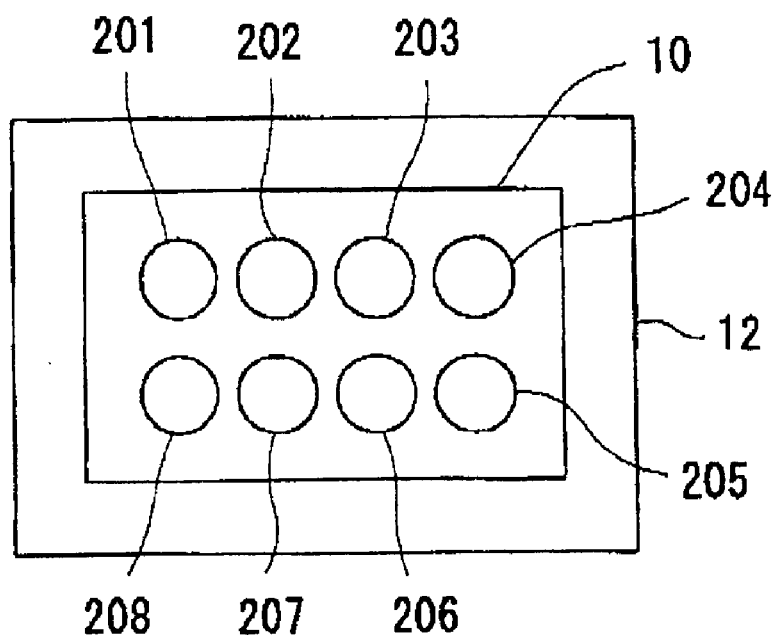
FIG. 5 is a view showing irradiation samples created on a positive film.

The operator observes the positive film 10 placed on the base 11 using the observation optical system 110 to perform alignment. Then, the laser beam is irradiated to create the first sample 201 as shown in FIG. 5. After inputting an irradiation condition for the next sample, the positive film 10 or the irradiation optical system 101 of the laser irradiation apparatus 1 is moved so that a sample 202, the second one, is created on a different position on the positive film 10. Hereafter, samples 203 to 208 are created on the positive film 10 in the same way.

The operator visually checks each of the samples 201 to 208 regarding their ablation conditions. When no abnormality is found in superimposition and uniformity in irradiated parts by visual checking, he inserts the positive film 10 into an unillustrated opening of the image scanner 20. Then, the image scanner 20 captures the eight samples 201 to 208 all together as a single image. The image photographed by the CCD 23 is stored in the memory 25. Next, he operates the analyzing device 30 to read and pass the image stored in the memory 25 to the device 30, and a condition of a change in the positive film 10, which means the ablation depth distribution in the present case, is analyzed.

Figure 6:
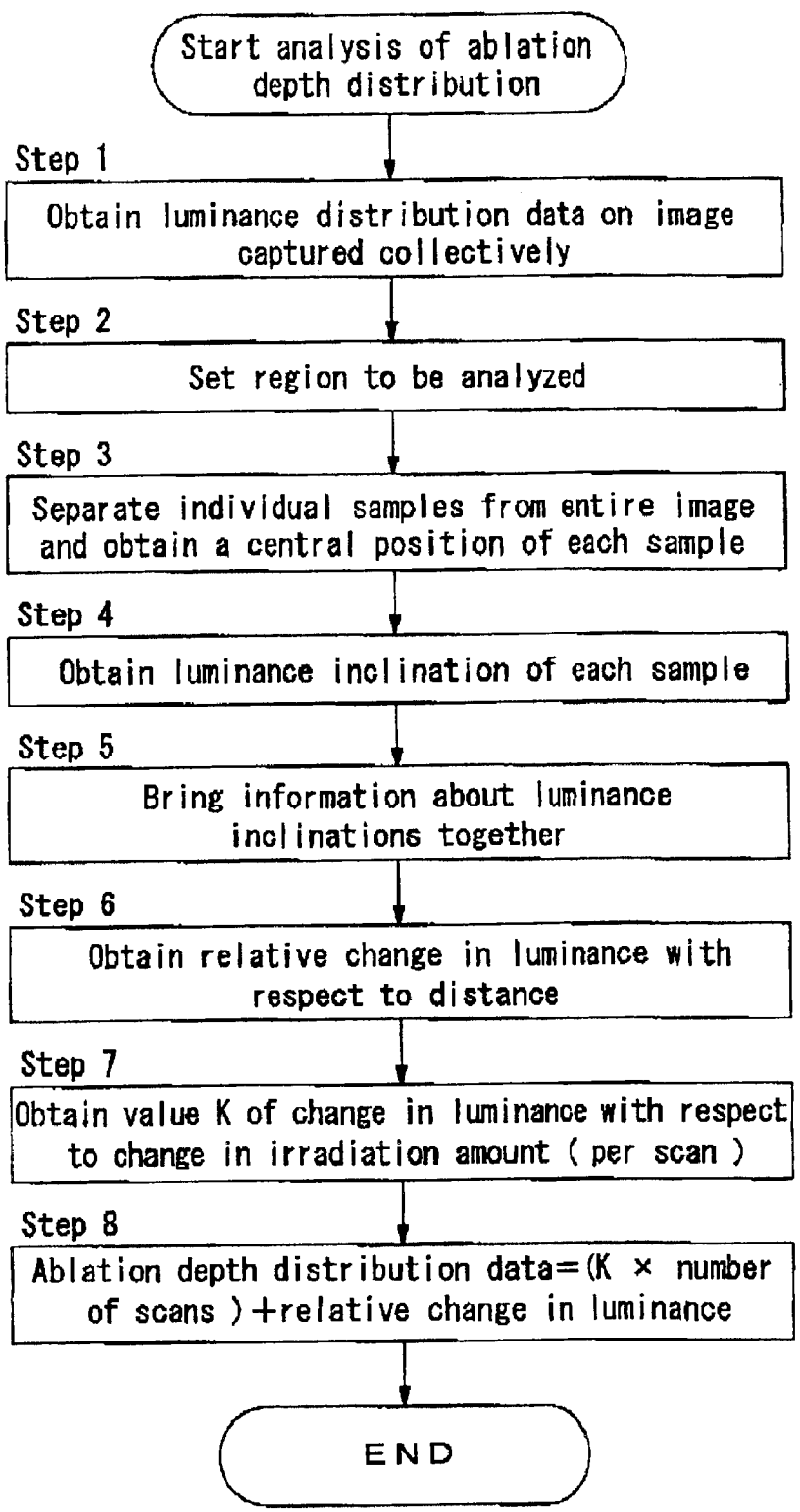
FIG. 6 is a flow chart describing steps to analyze an ablation depth distribution.

Now, a description will be given regarding the analysis of the ablation depth distribution (see FIG. 6).

<Step 1>

Figure 7:
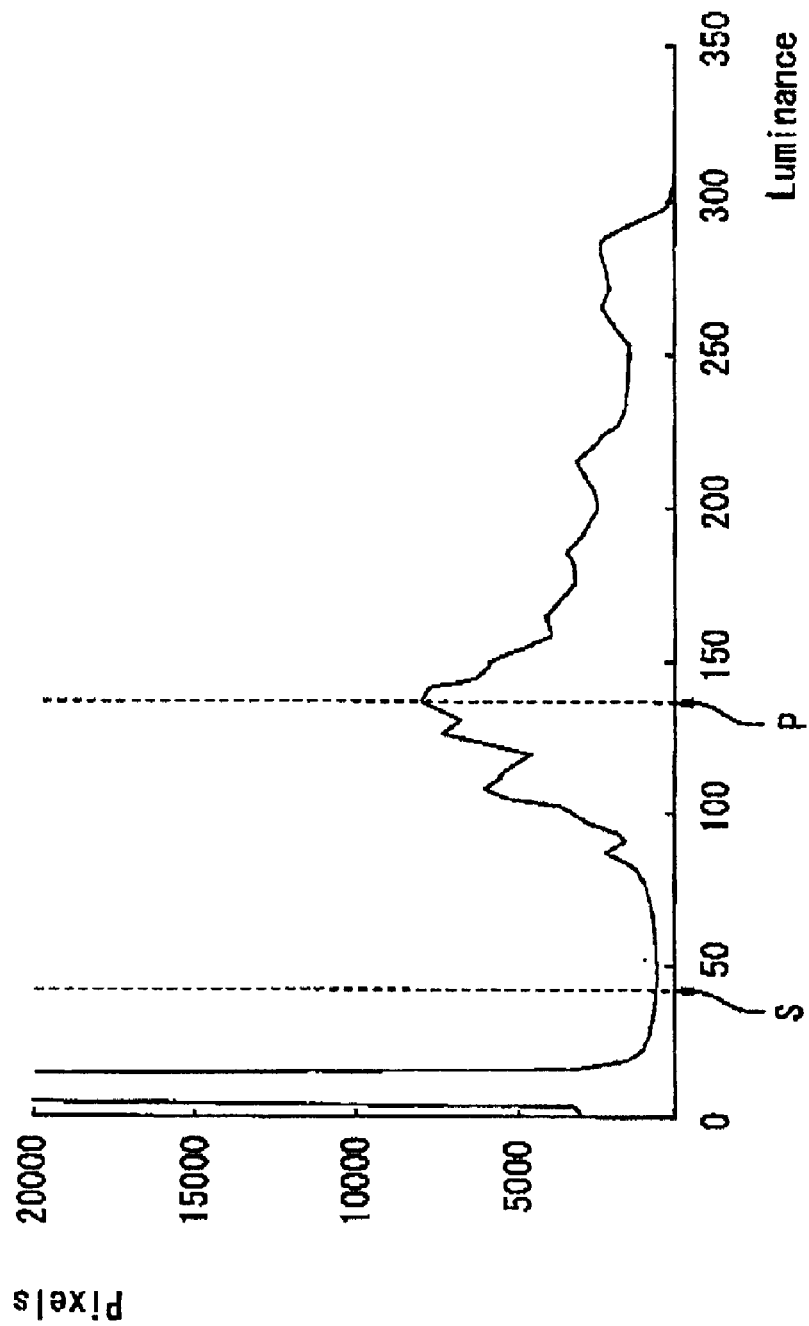
FIG. 7 is a luminance histogram showing luminance distribution data.

First, luminance distribution data of the entire image, including the images of the eight samples 201 to 208 captured all together, are obtained. It may be possible that the samples 201 to 208 are captured separately, but it is preferable that they be captured all together because the luminance distribution data are analyzed collectively, and each of the samples is analyzed based on the same reference. FIG. 7 is a luminance histogram showing the luminance distribution data, where the horizontal axis represents luminance, and the vertical axis represents the number of pixels. The image stored by the image scanner 20 is shown in three RGB colors, and the luminance is set at 256 levels multiplied by 3.

<Step 2>

In the luminance distribution data, there are more pixels in a region of the film 10 where the luminance does not change with respect to an increase in a laser irradiation amount (insensitive band). Then, the specific luminance region including a luminance part P which is a maximum value in the luminance distribution is considered as the insensitive band. At a high luminance side or a low luminance side from this insensitive band, a proper luminance region is specified to be analyzed. In the luminance histogram shown in FIG. 7, the region to be analyzed is the region of 54 levels on the high luminance side from the insensitive band. The positive film 10 is constituted of layers including each of color sensitive layers and a filter layer, and it has a layer with the insensitive band where the luminance does not change with respect to a change in the laser irradiation amount. This insensitive band is excluded from the region to be analyzed, and a region where the luminance changes with respect to a change in the laser irradiation amount is maximumly taken out. Incidentally, the luminance distribution is extremely high close to zero luminance and considered to be data on a region not to be ablated. Therefore, this region is also excluded from the analysis.

<Step 3>

Further, the regions to be analyzed of each of the samples 201 to 208 are individually separated from the entire image captured. Separating the regions to be analyzed from each of the samples 201 to 208 is carried out by binarizing the luminance at a determined threshhold level S at the low luminance side in the luminance histogram shown in FIG. 7. After that, a luminance barycenter is obtained for each sample, which is considered as a central position of each sample.

Figure 8:
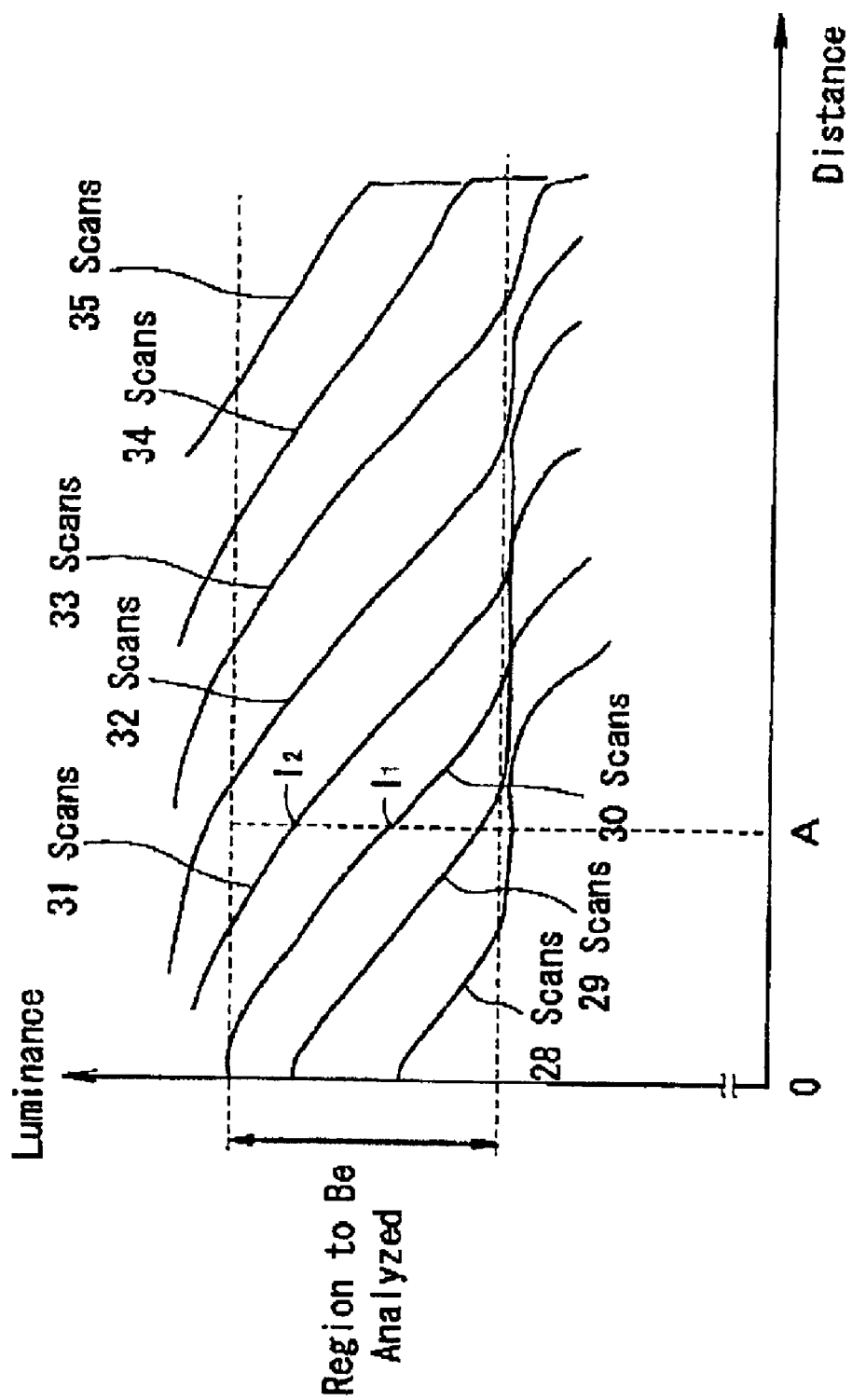
FIG. 8 is a graph showing a correlation between a distance from a central position and luminance of each irradiation sample.

<Step 4> a correlation between a distance from the central position and luminance of each sample is obtained (see FIG. 8), and a luminance inclination with respect to a certain unit distance (the number of dots of an image) is obtained. In this procedure, the luminance with respect to the distance of each sample is obtained as an average value. At this point, when a deviation of the luminance at the same distance is substantial, the device 30 notifies that maintenance is required due to a malfunction in the laser irradiation apparatus 1. In addition, for analysis of the ablation depth distribution, a certain laser irradiation amount, for example 30 scans, is specified as a standard. The luminance inclination of each sample is corrected by multiplying it by a coefficient of the following equation: 30 scans/the number of scans for the sample.

<Step 5>

As the luminance region specified in Step 2 is to be analyzed, information about luminance inclination obtained from all the samples is brought together. In the case where the information overlaps, the information having the larger absolute value of the luminance inclination is taken. when using one sample, it is difficult to obtain the information about luminance inclination for the entire region to be analyzed. However, bringing the information obtained from the plural samples together makes it possible to obtain the information about luminance inclination covering the entire region to be analyzed. Therefore, the number of the samples is determined such that a change in the luminance of the region to be analyzed may be obtained based on a size of the region to be analyzed, greatness of a change in the ablation depth distribution, and the luminance region.

<Step 6>

After the luminance inclination information about the entire region to be analyzed is obtained, it is integrated by each distance, whereby a relative change in luminance with respect to the distance from the central position can be obtained.

<Step 7>

Further, a value K of a change in luminance with respect to a change in the laser irradiation amount (per scan) is obtained from the correlation between the distance from the central position and luminance obtained from each sample (see FIG. 7). This value is calculated in the following way: First, a change in luminance according to a difference due to one scan is obtained for every distance in the region to be analyzed. For example, in FIG. 8, luminance I1 of 30 scans and luminance I2 of 31 scans are obtained at a certain distance A. A change in luminance according to a difference due to one scan at the distance A is obtained by subtracting I1 from I2. Then, this calculation is performed for every distance in the entire region to be analyzed, and the value obtained by adding the standard deviation to a mean value of all the changes in luminance is the value K.

<Step 8>

30 scans are specified as a standard for analyzing the ablation depth distribution, and the change in luminance of 30 scans is obtained by multiplying the value K of the change in luminance by 30. This value is specified as an offset value of a relative change in luminance obtained in Step 6. The value thus obtained is used as the ablation depth distribution data.

In the case where a single-layer material in which the gradation contrast change shows a constant relation with the change in the laser irradiation amount is used as a reference object, it is possible to obtain the ablation depth distribution data by analyzing one irradiation sample. In this case, reference data for the relation of the gradation contrast change with the ablation depth is obtained in advance so that the ablation depth distribution data are obtained.

Even in the case of using the single-layer material as the reference object for assessment, it is certainly possible to obtain the ablation depth distribution data in the same way as stated above, if there are at least two irradiation samples which have received different laser irradiation amounts. In this situation, however, it is preferable to use an image capturing (obtaining) device having a high luminance resolving power.

When the operator receives the ablation depth distribution data thus obtained, he confirms whether its uniformity falls within a tolerant bound, or not. The confirmation can be made using the analyzing device 30. In the case where the ablation depth distribution data are not uniform, the operator inputs the ablation depth distribution data having been analyzed to the control device 120 of the laser irradiation apparatus 1 directly or using the input device 125. The control device 120 calculates control data on the travel velocity of the mirror 104 based on the inputted data. That is, the control device 120 obtains data for changing the travel velocity of the mirror 104 from a ratio of a change in the ablation depth relative to the distance from the irradiation central position, as the control data of the travel velocity of the mirror 104 at the time of creating the irradiation sample.

When calculation of the control data by the control device 120 is completed, the ablation depth distribution is assessed again by irradiating the laser beam on the positive film 10 for confirming uniformity of the irradiation energy.

Up to this point, the control data of the laser irradiation apparatus 1 is the travel velocity of the mirror 104, but it is possible to employ the method of controlling the output of the laser light source 102 itself or the method of controlling laser irradiation time. Further, needless to say, assessment of laser irradiation intensity may be carried out not only for approximately uniformly ablating the object to be irradiated, but also for other forms.

In addition, The embodiment described above is presented by giving an example of the laser beam causing ablation on the object to be irradiated, but various laser beams such as laser beams causing coagulation under the action of heat may be employed. When using a laser beam with a wavelength which causes fundus coagulation, an operator may use a reference object in which a quantity of transmitted light of illumination light changes under the action of coagulation, and may analyze the condition of the change.

As described so far, the present invention is capable of accurately assessing irradiation intensity of a laser beam, with a relatively uncomplicated mechanism. Accordingly, it is possible to control a variation in a distribution of irradiation energy density occurring in each laser irradiation apparatus.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. An apparatus for assessing irradiation intensity of a laser beam comprising:
   a reference object on which photo-ablation is caused by irradiating an ultraviolet laser beam for ablation and on which an irradiation region is formed by an ultraviolet laser processing device which processes the reference object in a condition of ablating a predetermined irradiation region to a uniform depth, the reference object having a layer in which a transmitting quantity of illumination light changes in accordance with a thickness;

an image obtaining device which obtains an image having information on a gradation contrast change based on the transmitting quantity of the illumination light transmitted through respective positions in the irradiation region of the reference object by projecting the illumination light onto the reference object on which the irradiation region has been formed; and an assessing device which assesses appropriateness of irradiation intensity distribution of the ultraviolet laser processing device based on whether the gradation contrast change is in a permissible range by analyzing information on a luminance change in the irradiation region of the image.

2. The apparatus for assessing irradiation intensity of a laser beam according to claim 1, wherein the irradiation region is formed by repeatedly providing a plurality of uniform irradiation to the reference object taking a minimum ablation depth as a unit, the image obtaining device obtains a plurality of the images having information on the gradation contrast change which are different in the number of irradiation, and the assessing device combines the information on the luminance change in the irradiation region of each of the images to obtain information on the irradiation intensity distribution for a whole region to be analyzed.

3. The apparatus for assessing irradiation intensity of a laser beam according to claim 1, wherein the reference object includes a commercially available film for photographing.

4. A laser beam irradiation system comprising:

an irradiation optical system for irradiating an ultraviolet laser beam for ablation onto an object to be irradiated;

a reference object on which photo-ablation is caused by irradiating the laser beam and on which an irradiation region is formed by the irradiation optical system which irradiates the laser beam onto the reference object in a condition of ablating a predetermined irradiation region to a uniform depth, the reference object having a layer in which a transmitting quantity of illumination light changes in accordance with a thickness;

an image obtaining device which obtains an image having information on a gradation contrast change based on the transmitting quantity of the illumination light transmitted through respective positions in the irradiation region of the reference object by projecting the illumination light onto the reference object on which the irradiation region has been formed;

an assessing device which assesses appropriateness of irradiation intensity distribution of the irradiation optical system based on whether the gradation contrast change is in a permissible range by analyzing information on a luminance change in the irradiation region of the image; and a control device which obtains control data for the system so that the object to be irradiated achieves a condition of a desired change based on an analytical result from the assessing device.

5. The laser beam irradiation system according to claim 4, further comprising a laser scanning unit which is arranged in the irradiation optical system and scans the object to be irradiated by the laser beam, and wherein the control device obtains the control data for the laser scanning unit.

6. The laser beam irradiation system according to claim 4, wherein the irradiation region is formed by repeatedly providing a plurality of uniform irradiation to the reference object taking a minimum ablation depth as a unit, the image obtaining device obtains a plurality of the images having information on the gradation contrast change which are different in the number of irradiation, and the assessing device combines the information on the luminance change in the irradiation region of each of the images to obtain information on the irradiation intensity distribution for a whole region to be analyzed.

7. The laser beam irradiation system according to claim 4, wherein the reference object includes a commercially available film for photographing.

8. A method for assessing irradiation intensity of a laser beam including steps of:

forming an irradiation region on a reference object on which photo-ablation is caused by irradiating an ultraviolet laser beam for ablation, the reference object having a layer in which a transmitting quantity of illumination light changes in accordance with a thickness, by processing the reference object in a condition of ablating a predetermined irradiation region to a uniform depth with an ultraviolet laser processing device;

obtaining an image having information on a gradation contrast change based on the transmitting quantity of the illumination light transmitted through respective positions in the irradiation region of the reference object by projecting the illumination light onto the reference object on which the irradiation region has been formed; and assessing appropriateness of irradiation intensity distribution of the ultraviolet laser processing device based on whether the gradation contrast change is in a permissible range by analyzing information on a luminance change in the irradiation region of the image.

9. The method for assessing irradiation intensity of the laser beam according to claim 8, wherein the reference object includes a commercially available film for photographing.

10. The method for assessing irradiation intensity of the laser beam according to claim 8, wherein forming the irradiation region includes repeatedly providing a plurality of uniform irradiation to the reference object taking a minimum ablation depth as a unit, obtaining the image having the information on the gradation contrast change includes obtaining a plurality of the images having information on the gradation contrast change which are different in the number of irradiation, and assessing appropriateness of the irradiation intensity distribution includes combining the information on the luminance change in the irradiation region of each of the images to obtain information on the irradiation intensity distribution for a whole region to be analyzed.

* * * * *